United States Patent
Lindquist et al.

[11] Patent Number: 5,454,802
[45] Date of Patent: Oct. 3, 1995

[54] SANITARY NAPKIN OR INCONTINENCE GUARD

[75] Inventors: Bengt Lindquist, Lerum; Eva Vastag, Härryda, both of Sweden

[73] Assignee: Mölnlycke AB, Göteborg, Sweden

[21] Appl. No.: 118,693

[22] Filed: Sep. 10, 1993

Related U.S. Application Data

[63] Continuation of Ser. No. 838,755, May 20, 1992, abandoned.

[30] Foreign Application Priority Data

Sep. 20, 1989 [SE] Sweden ................... 8903090

[51] Int. Cl.$^6$ ............................... A61F 13/15
[52] U.S. Cl. ............................... 604/385.1
[58] Field of Search ........................ 604/385.1

[56] References Cited

U.S. PATENT DOCUMENTS

| | | | |
|---|---|---|---|
| 2,747,575 | 5/1956 | Mercer. | |
| 4,490,147 | 12/1984 | Pierce et al.. | |
| 4,595,392 | 6/1986 | Johnson et al. | 604/385.1 |
| 4,631,062 | 12/1986 | Lassen et al. | 604/385.1 |
| 4,743,245 | 5/1988 | Lassen et al. | 604/385.1 |
| 4,804,380 | 2/1989 | Lassen et al. | 604/385.1 |
| 4,848,572 | 7/1989 | Herrera | 206/440 |
| 5,092,860 | 3/1992 | Pigneul | 604/385.1 |
| 5,098,422 | 3/1992 | Davis et al. | 604/385.1 |
| 5,127,911 | 7/1992 | Baharav | 604/385.1 |

FOREIGN PATENT DOCUMENTS

| | | | |
|---|---|---|---|
| 91412 | 10/1983 | European Pat. Off.. | |
| 0270058 | 6/1988 | European Pat. Off.. | |
| 0304644 | 3/1989 | European Pat. Off.. | |
| 389023 | 9/1990 | European Pat. Off.. | |
| 2653328 | 4/1991 | France | 604/385.1 |
| 212150 | 7/1988 | New Zealand. | |
| 157046 | 1/1988 | Norway. | |
| 163164 | 4/1990 | Norway. | |
| 8804547 | 6/1988 | WIPO. | |

*Primary Examiner*—Jerome L. Kruter
*Attorney, Agent, or Firm*—Burns, Doane, Swecker & Mathis

[57] ABSTRACT

An absorbent article, such as a sanitary napkin or incontinence guard, comprises a liquid-impermeable surface layer which is remote from the wearer when the article is worn, a liquid-permeable surface layer which faces towards the wearer in use, and an absorbent pad which is contained between the two surface layers. The absorbent pad is arched in a transverse direction, at least at its center part, and therewith exhibits a convex surface on the side of the pad which faces the wearer in use. The edges of the article are restrained from flexing toward the liquid-permeable surface, and the transverse arch is maintained by a restraining device attached to the longitudinal edges of the article.

10 Claims, 2 Drawing Sheets

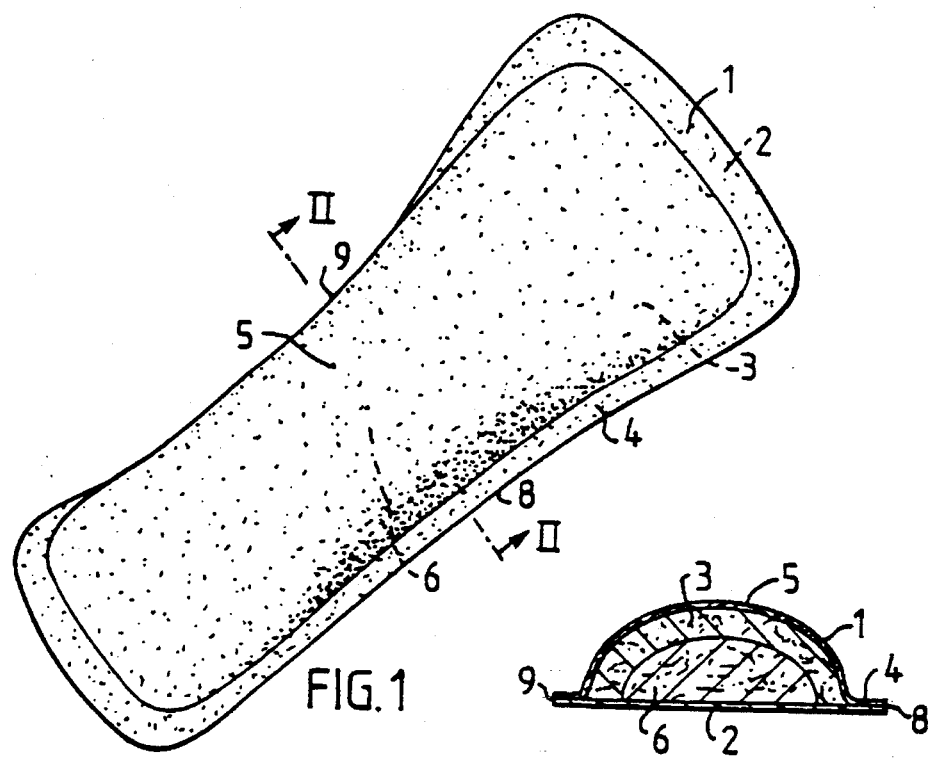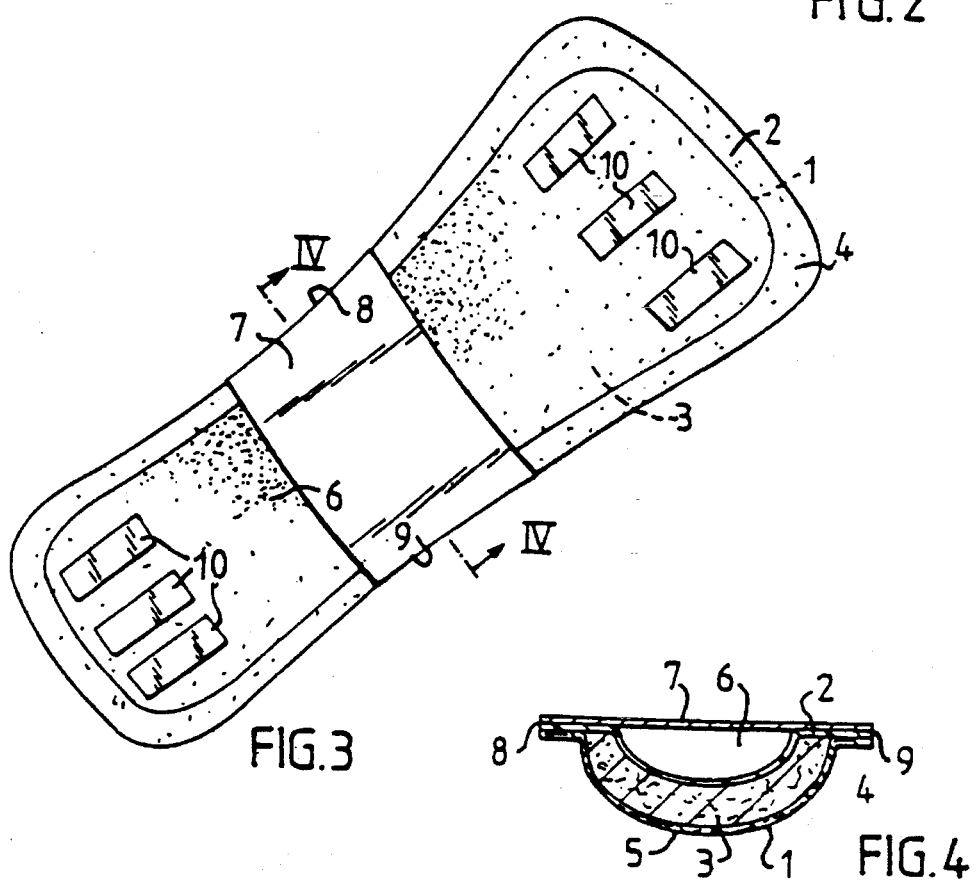

SANITARY NAPKIN OR INCONTINENCE GUARD

This application is a continuation of application Ser. No. 07/838,755, filed May 20, 1992 now abandoned.

BACKGROUND OF THE INVENTION

The present invention relates to an absorbent article, such as a sanitary napkin or an incontinence guard, comprising a liquid-impermeable casing layer or backing sheet which is remote from the wearer in use, a liquid-permeable surface layer which faces towards the wearer in use, and an absorbent pad contained between the two surface layers or sheets.

Such articles are preferably narrow and are intended to be carried in the crotch part of a pair of underpants or panties, the article normally being secured to the panties by means of pressure-sensitive adhesive provided on the liquid-impermeable rear side of the article.

The primary drawback with absorbent articles of this kind is that they too often leak along the side edges of the article, therewith soiling the undergarment. The most common reason for leakage along the side edges of such an article is because during use the article will become deformed and fold or crumple in its long direction. It is not unusual for the side edges of the article and a part of its liquid-impermeable backing sheet to fold-in over its liquid-permeable front layer. Naturally, this will considerably reduce the liquid absorbency of the article, since only a narrow liquid-permeable part will remain between the inwardly folded edge parts.

It is known to reduce the risk of this type of lateral leakage resulting from deformation of the article in use, by forming with the aid of air-deposition techniques an absorbent pad which exhibits a raised part which is intended to lie against the genitals of the wearer when the article is in use. Secreted body fluid is sucked immediately into the article, since the article is in close abutment with the body of the wearer. Furthermore, the pre-shaped article will only be slightly deformed during use.

Although a pre-shaped article of this kind has been found to function satisfactorily with respect to leakage, it unfortunately has other drawbacks. The raised portion of the article is experienced by the wearer as being hard and uncomfortable and constitutes an obstacle or hinder when cycling, for instance.

SE 8605498-8 describes a sanitary napkin which has a soft, raised part on the side of the article that faces towards the wearer in use. This raised part is created by incorporating pre-tensioned elastification in the liquid-impermeable surface layer on the rear side of the napkin. Although a napkin of this kind is soft and comfortable to wear, it is not particularly attractive from an aesthetic aspect when worn, since the elastication draws or gathers together the liquid-impermeable layer of the napkin, such that even an unused napkin appears to be wrinkled and handled. Furthermore, it is almost impossible to provide adhesive fastener surfaces on the wrinkled undersurface of the napkin, and consequently it is necessary to support the napkin by means of some form of holder or girdle. This necessity is hardly acceptable to present-day users of such absorbent articles, however, since it has been customary for such users to simply secure the article directly to a pair of conventional underpants or panties.

OBJECTS AND SUMMARY

However, the present invention provides an absorbent article of the kind defined in the introduction which totally avoids the drawbacks of known articles of this kind. An article configured in accordance with the invention is primarily characterized in that the absorbent pad is arched in its cross-direction, at least at its centre part, and therewith exhibits a convex surface on the side of the article which faces towards the wearer in use, and in that means are provided for preventing the distance between the side edges of the absorbent pad at its arched part from exceeding a determined value which is smaller than the width of the liquid-permeable surface layer in a flat state.

The fact that the longitudinally extending side edges of an absorbent article are prevented from moving apart by more than a predetermined distance, as in accordance with the present invention, affords a number of advantages. For instance, it is impossible for the side edges of the article to fold in over the liquid-permeable surface layer of said article, since the side-edge restraining locking facility obtained with said article functions to urge the side edges to bend outwardly in the opposite direction. Furthermore, the side-edge restraining facility can be said to constitute a method of controlling the shaping and bending of the article while it is worn, so that, in use, the article will bend and flex so as to lie constantly against the body of the wearer. This enables secreted body liquid to be drawn directly into the absorbent pad and eliminates the risk of leakage past the side edges of the article. An article constructed in accordance with the invention contains essentially the same amount of absorbent material at its centre part as a conventional, flat absorbent article. This means that the article will be more responsive to the effect of external pressures than the earlier known napkins with which the raised portion is created by agglomorating absorbent material at the centre part of the napkin. This higher degree of compressibility of an inventive article means that the article will adapt more readily to the space between the thighs of the wearer. The article will therewith be soft and comfortable to the wearer and can be worn discretely.

An absorbent article having a soft arched portion and mutually locked side edges can be manufactured in a number of different ways. For instance, an arched absorbent body can be produced by building-up a commensurate configuration of absorbent material or by bending or arching a conventional, flat absorbent body. The maximum smallest distance between the opposing side edges of the absorbent pad is made permanent, either by making the liquid-impermeable layer on the rear side of the article smaller than the liquid-permeable layer on the front side of the article, or by applying separate locking tape which mutually connects the side edges of said article. This locking tape may, for instance, consist of shrink film or a plastic tape which is extended transversely over the width of the article, suitably at its centre part.

In those instances when the inventive absorbent article is produced from a flat absorbent pad which is subsequently arched, said pad may initially be straight or formed with a slightly wider centre part. In this latter case, the arched portion will contain more absorbent material. It is important, however, that the ultimate arched portion does not contain so much absorbent material as to detract from its softness and comfort in wear.

It has been found unsuitable to locate adhesive for securing the article to the wearer's underpants or panties immediately beneath the actual arched portion itself. Instead, the adhesive is preferably located along the end parts of the article, so that the article will conform to the contours of the wearer's body to the greatest possible extent.

The invention will now be described in more detail with reference to an exemplifying embodiment of an inventive absorbent article and with reference to the accompanying drawings.

BRIEF DESCRIPTION OF THE DRAWINGS

FIG. 1 of the drawings illustrates a first embodiment of an inventive sanitary napkin, seen from the side thereof which faces the wearer in use.

FIG. 2 is a cross-sectional view of the sanitary napkin shown in FIG. 1, taken on the line II—II.

FIG. 3 illustrates a second embodiment of an inventive sanitary napkin, seen from the side which lies remote from the wearer in use.

FIG. 4 is a sectional view of the sanitary napkin shown in FIG. 3, taken on the line IV—IV.

DETAILED DESCRIPTION OF THE PREFERRED EMBODIMENTS

Figure 5:
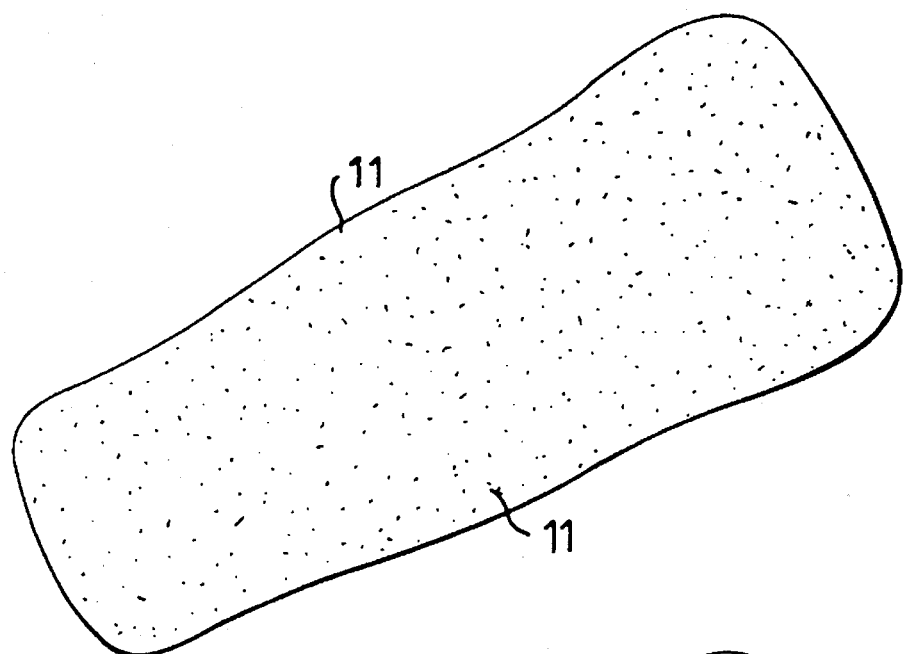
FIG. 5 illustrates a flat absorbent pad intended for a sanitary napkin according to a third embodiment of the invention.

The sanitary napkin illustrated in FIGS. 1 and 2 includes a first liquid-permeable casing layer 1 on the side of the napkin which faces the wearer in use. The napkin also includes a liquid-impermeable second casing layer 2 on the side of the napkin remote from the wearer in use, and an absorbent pad or body 3, made for instance of cellulose fluff, which is contained between the two casing layers 1 and 2. The two casing layers 1, 2 extend slightly beyond the absorbent pad and the outwardly protruding casing parts 4 are mutually joined around the full circumference of the absorbent pad 3.

Because the liquid-impermeable casing layer 2 is narrower than the liquid-permeable casing layer 1, the absorbent pad 3 is held arched and presents a convex surface 5 on that side of the pad which faces towards the liquid-permeable outer layer 1. Located between the absorbent pad 3 and the liquid-impermeable casing layer 2 is a cavity 6 which is more or less well defined. The size of the cavity 6 depends on the extent to which the absorbent pad 3 is arched and also on the choice of absorbent material. A well integrated absorbent pad will provide a more specifically defined cavity, whereas non-bound cellulose fluff, for instance, will tend to fill the cavity almost completely. This is primarily the case when the napkin is worn, since the napkin is then compressed between the thighs of the wearer. Cellulose fluff is not springy and therefore has practically no intrinsic restoring capacity. Consequently, an absorbent pad which is made of such material is unable to return to its original shape subsequent to being deformed. When no such constant deformation is desired, the absorbent pad may, of course, include a stiffening layer or elastic restoring means, for instance in the form of a plastic foam layer. The absorbent pad may also include so-called superabsorbents, these being materials capable of absorbing body fluid in quantities corresponding to several times their own weight. Examples of such materials are polyacrylates and modified cellulose. Superabsorbents may also be placed in the napkin cavity and there function to bind body fluid at a location remote from the body of the wearer.

The sanitary napkin illustrated in FIGS. 3 and 4 has essentially the same contruction as the sanitary napkin illustrated in FIGS. 1 and 2. Consequently, similar napkin members have been identified with reference signs identical to those used in FIG. 1. The casing layers 1 and 2 of this embodiment, however, have substantially the same geometric extension. In this case, the napkin is retained in its arched state with the aid of a restraining strip 7 attached to the centre part of the napkin, between the two side edges 8, 9 thereof. The restraining tape 7 may be attached to the liquid-impermeable casing layer 2 either by gluing or welding said tape. In order to achieve the desired napkin configuration, it has been found necessary for the restraining tape 7 to extend over at least 1/10 of the length of the absorbent pad 3 and preferably over at least 1/2 of said length.

The napkin embodiment illustrated in FIGS. 3 and 4 also exhibits pressure-sensitive adhesive surfaces at the two end parts of the liquid-impermeable casing layer 2. The adhesive surfaces 10 are intended to function as means for securing the napkin to a pair of underpants or like undergarment and said surfaces are preferably covered with protective tapes coated with a release agent, these protective tapes being removed before use. As before mentioned, an inventive napkin is preferably secured to the underpants of the wearer solely at the end parts of the napkin in use. This enables the napkin to conform effectively to the body of the wearer.

The absorbent body 3 illustrated in FIG. 5 is flat and has a relatively broad centre part 11. Consequently, the centre part of the finished, arched absorbent pad will have a higher concentration of absorbent material, which can be beneficial, for instance, when the pad is used for an incontinence guard or in a sanitary napkin where menstruation is heavy and the pad must therefore be capable of absorbing a relatively large flow of liquid over a short time period.

Figure 6:
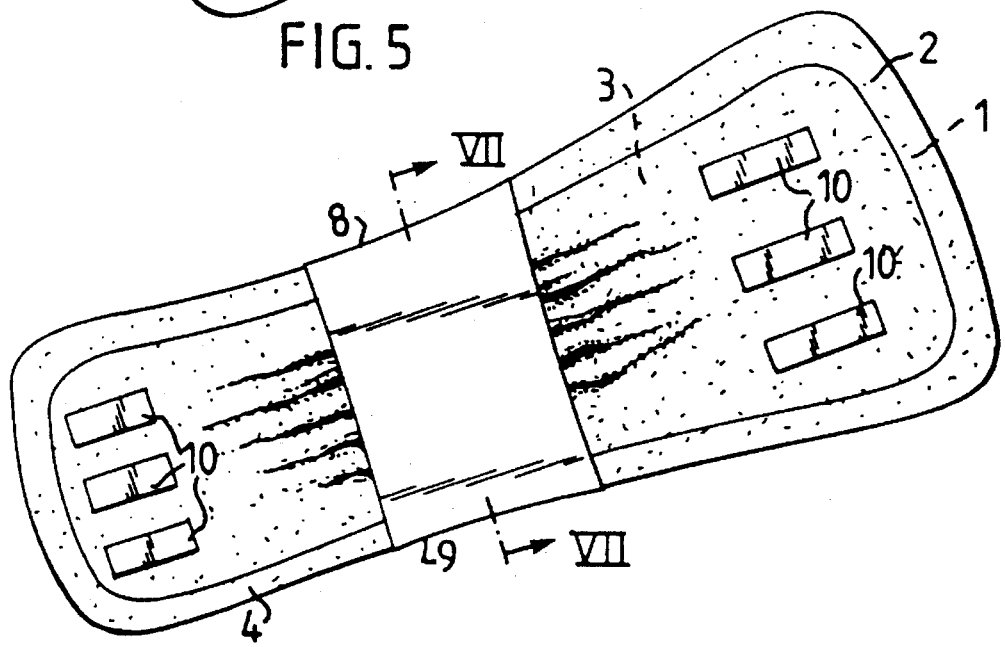
FIG. 6 illustrates a fourth embodiment of an inventive sanitary napkin, seen from the side of the napkin remote from the wear in use.
Figure 7:
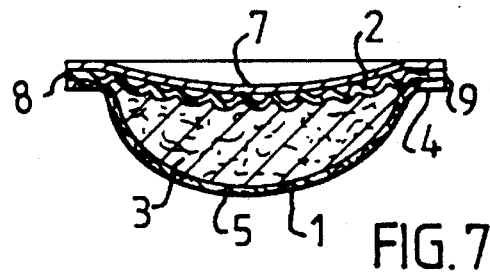
FIG. 7 is a sectional view of the sanitary napkin shown in FIG. 6, taken on the line VII—VII.

The napkin illustrated in FIG. 6 and 7 also has essentially the same construction as the earlier described napkins. The napkin according to FIG. 6 and 7, however, distinguishes from the earlier described napkins in that it includes a restraining tape 7 of heat-shrinkable material. The restraining tape 7 is attached to the liquid-impermeable casing layer 2 across the whole of its surface lying against said layer 2. The restraining tape 7 is fastened to a flat napkin and thereafter caused to shrink or contract and therewith arch the napkin. Since the liquid-impermeable casing material 2 is not shrinkable, it will be drawn or gathered together behind the restraining tape.

As with the case of the napkin of the FIG. 3 and 4 embodiment, it is important that the restraining tape 7 extends over at least 1/10 of the length of the absorbent pad, and preferably over more than 1/2 of said length. Naturally, the whole of the liquid-impermeable casing layer can be made of a shrinkable material. This will then obviate the need for an additional restraining tape.

The restraining tape may also be positioned between two casing layers, for instance a plastic film and a fabric layer. This improves fixation of the restraining tape. Furthermore, the fabric layer will enhance the friction acting between the napkin and the underpants of the wearer.

The aforedescribed exemplifying embodiments do not limit the scope of the invention, since further modifications are conceivable within the scope of the following claims.

We claim:

1. An absorbent article, comprising:
    a first liquid-impermeable casing layer having two longitudinal edges and two transverse ends;
    a second liquid-permeable casing layer having two longitudinal edges and two transverse ends;

an absorbent pad contained between said first and second casing layers;

said respective longitudinal edges and transverse ends of said casing layers being joined so as to form longitudinal seams and transverse seam, respectively;

said absorbent pad having a generally oblong shape, two longitudinally extending sides, a front transverse edge, and a rear transverse edge, a center part located between said front and rear edges, wherein at least said center part is arched transversely across said sides to form a convex surface in a direction of said second casing layer; and restraining means connected to both longitudinal seams and positioned adjacent to said first casing layer for restraining said longitudinal seams from flexing in a direction towards said second layer, and for maintaining said longitudinal seams in a predetermined orientation and maximum spacing relative to each other;

wherein the restraining means comprises a material strip which at a center part of the article is attached at least to the longitudinal seams of the liquid-impermeable casing layer and extends between said two longitudinal seams.

2. An absorbent article according to claim 1, wherein the material strip is attached solely to the longitudinal edges of the liquid-impermeable layer, the material strip being narrower than a distance between the longitudinal seams of said article when the article is in a flat state, whereby the article will exhibit a convex surface in the direction of the liquid-permeable layer.

3. An absorbent article according to claim 1, wherein the material strip consists of a shrinkable material and is attached to the liquid-impermeable casing layer covering said liquid-impermeable layer, wherein in a shrunk or contracted state the material strip is shorter than a distance between the longitudinal seams of the article when said article is in a flat state, whereby the article exhibits a convex surface on the liquid-permeable casing side of said article.

4. An absorbent article according to claim 1, wherein the material strip extends over at least 1/10 of the longitudinal seams of the absorbent pad.

5. An absorbent article according to claim 1, wherein the material strip extends over at least 1/7 of said longitudinal seams.

6. An absorbent article, comprising:

a first liquid-impermeable casing layer having two longitudinal edges and two transverse ends;

a second liquid-permeable casing layer having two longitudinal edges and two transverse ends;

an absorbent pad contained between said first and second casing layers;

said respective longitudinal edges and transverse ends of said casing layers being joined so as to form longitudinal seams and transverse seams, respectively;

said absorbent pad having a generally oblong shape, two longitudinally extending sides, a front transverse edge, and a rear transverse edge, a center part located between said front and rear edges, wherein at least said center part is arched transversely across said sides to form a convex surface in a direction of said second casing layer; and, restraining means connected to both longitudinal seams and positioned adjacent to said first casing layer for maintaining said arched shape by restraining said longitudinal seams to a maximum spacing relative to each other, restraining and longitudinal seams from flexing in a direction towards said second layer, and for maintaining said longitudinal seams in a predetermined orientation.

7. An absorbent article according to claim 6, wherein the liquid-impermeable casing layer consists of shrinkable material.

8. An absorbent article according to claim 6, wherein the maximum spacing is less than a width of said liquid-permeable layer at the center part.

9. An absorbent article, comprising:

a first liquid-impermeable casing layer having two longitudinal edges and two transverse ends;

a second liquid-permeable casing layer having two longitudinal edges and two transverse ends;

an absorbent pad contained between said first and second casing layers;

said respective longitudinal edges and transverse ends of said casing layers being joined so as to form longitudinal seams and transverse seams, respectively;

said absorbent pad having a generally oblong shape, two longitudinally extending sides, a front transverse edge, and a rear transverse edge, a center part located between said front and rear edges, wherein at least said center part is arched transversely across said sides to form a convex surface in a direction of said second casing layer; and a portion of said first liquid-impermeable casing layer includes restraining means connected to both longitudinal seams for maintaining said arched shape by restraining said longitudinal seams to a maximum spacing relative to each other, for restraining said longitudinal seams from flexing in a direction towards said second layer, and for maintaining said longitudinal seams in a predetermined orientation;

said liquid-impermeable casing layer being transversely shorter than the liquid-permeable casing layer, at least at a center part of the article.

10. An absorbent article according to claim 9, wherein the maximum spacing is less than a width of said liquid-permeable layer at the center part.

* * * * *